United States Patent [19]
Hargis et al.

[11] Patent Number: 6,110,455
[45] Date of Patent: Aug. 29, 2000

[54] METHOD FOR ENCOURAGING POULTRY TO DISTRIBUTE AND INGEST COMPETITIVE EXCLUSION PRODUCTS

[75] Inventors: Billy Marshall Hargis; Denise Yvette Caldwell, both of College Station, Tex.

[73] Assignee: MS Bioscience, Madison, Wis.

[21] Appl. No.: 09/234,552

[22] Filed: Jan. 20, 1999

[51] Int. Cl.[7] .......................... A01N 63/00; A01N 65/00; A23C 9/12

[52] U.S. Cl. .................... 424/93.1; 424/93.45; 424/93.3; 424/93.46; 424/93.47; 424/93.48; 426/2; 426/61

[58] Field of Search ................................ 424/93.1, 93.45, 424/93.3, 93.46, 93.47, 93.48; 426/2, 61

[56] References Cited

U.S. PATENT DOCUMENTS

| | | |
|---|---|---|
| 4,335,107 | 6/1982 | Snoeyenbos et al. . |
| 4,689,226 | 8/1987 | Nurmi et al. . |
| 5,114,708 | 5/1992 | Hunter et al. . |
| 5,132,288 | 7/1992 | Johnson et al. . |
| 5,234,683 | 8/1993 | Hunter et al. . |
| 5,308,615 | 5/1994 | DeLoach et al. . |
| 5,340,577 | 8/1994 | Nisbet et al. . |
| 5,451,400 | 9/1995 | Stern et al. . |
| 5,466,445 | 11/1995 | Hunter . |
| 5,478,557 | 12/1995 | Nisbet et al. . |

FOREIGN PATENT DOCUMENTS

WO 98/02523 A1 1/1998 WIPO .

OTHER PUBLICATIONS

Young, S.D. et al., Effects of Photointensity and Color on Preening–Associated Ingestion of Spray–Applied Biologics in Neonatal Chicks, Poultry Science, (1988) vol. 77, No. Suppl. 1, pp. 94. Meeting Info.: Eighty–seventh Annual Meeting of the Poultry Sc, Aug. 1998.

Caldwell, D.Y. et al., Effects of Photointensity, Sound and Ambient Temperature on Preening Behavior and Ingestion of Spray–Applied Biologics, Poultry Science (1988) vol. 77, No. Suppl. 1, pp. 119. Meeting Info.: Nineteenth Annual Meeting of the Southern, Jan. 1998.

Hume, M.E. et al., Reduction of caecal Listeria monocytogenes in Leghorn chicks following treatment with a competitive exclusion culture (PREEMPT–trademark), Letters in Applied Microbiology, vol. 26: 432–436, 1988.

Corrier, D.E. et al., Competitive Exclusion of Salmonella enteritidis in Leghorn Chicks: Comparison of Treatment by Crop Gavage, Drinking Water, Spray, or Lyophilized Alginate Beads, Avian Diseases, 38: 297–303, 1994.

Gould, J.L. et al., Biological Science, pp. 1094–1095, W.W.Norton & Co., New York, NY, 1996.

Compton et al., Compton Interactive Encyclopedia, T.L.C. Properties, Inc., 1997.

*Primary Examiner*—Leon B. Lankford, Jr.
*Assistant Examiner*—Michele C. Flood
*Attorney, Agent, or Firm*—Philip Summa, P.A.

[57] ABSTRACT

A method is disclosed for increasing the rate at which young poultry will ingest beneficial probiotic compositions effective against bacteria such as salmonella. The method includes the steps of maintaining a flat containing a plurality of chicks at a first position under an ambient light intensity for a period sufficient for the chicks to acclimate to the ambient light intensity, transferring the flat and the chicks therein to a second position where the light intensity to which the chicks are being exposed is at a predetermined higher intensity that the ambient intensity, distributing a competitive exclusion product onto the flat of chicks while the flat and chicks therein are being exposed to the higher intensity light, immediately thereafter transferring the flat and the chicks therein to a third position where the chicks are exposed to an intermediate light intensity that is greater than the ambient intensity but less than the predetermined high intensity, and maintaining the flat and the chicks therein in the third position and exposed to the intermediate light intensity for a period substantially equivalent to the effective lifetime of the competitive exclusion product.

26 Claims, 7 Drawing Sheets

METHOD FOR ENCOURAGING POULTRY TO DISTRIBUTE AND INGEST COMPETITIVE EXCLUSION PRODUCTS

FIELD OF THE INVENTION

The present invention relates to methods of distributing probiotic compositions in poultry, and in particular relates to a method of enhancing the degree to which chicks will distribute and take up competitive exclusion compositions effective against salmonella bacteria.

BACKGROUND OF THE INVENTION

Salmonella has become unfortunately recognized as a serious health concern in food products intended for human consumption. Salmonella is of particular concern in meat products because of its potential presence in livestock, particularly cattle, swine and poultry, at various stages in their growth cycle. Although the risk of salmonella-caused illness in humans can be greatly reduced—and indeed eliminated—by proper handling techniques during food preparation and storage (both commercial and domestic), eliminating salmonella at the earliest possible point in the food production chain remains a desirable goal.

To this effect, significant progress has been made in recent years in fighting salmonella using probiotic techniques and compositions rather than antibiotics or other pharmaceutical compositions. As used herein, the term "probiotic" refers to compositions or organisms that do not attack the salmonella bacteria as would a pharmaceutical composition, but rather that replace the salmonella in the host animal with a more beneficial bacteria, or with a bacteria that simply prevents the salmonella bacteria from gaining a useful foothold from which it can continue to contaminate, or indeed increase its contamination of, the host animal and the animals to which the host spreads the salmonella. Such compositions are also referred to as "competitive exclusion" products.

Exemplary probiotics for use with poultry are set forth in U.S. Pat. Nos. 5,308,615; 5,340,577; and 5,478,557, the contents of which are incorporated entirely herein by reference.

In order to work successfully, however, the probiotic must be taken up by the target animal, in this case poultry. For example, the probiotics set forth in the '615, '577, and '557 patents must be ingested by poultry in a manner that places the probiotic composition in the digestive tract. Conventionally, this can be done using oral gavage, or by mixing the probiotic with feedstuffs or drinking water that the poultry are expected to ingest. Furthermore, the nature of probiotics is such that they are most effective—and in some cases solely effective—when ingested shortly after an animal's birth. Stated differently, because in most cases the probiotic is a preventative measure, it must be in place in the animal's digestive tract before salmonella can gain a foothold.

Each technique presents certain problems. Oral gavage is the most effective technique: every bird gets the correct dose. Nevertheless, oral gavage requires that each individual bird be handled and fed the probiotic. To date such handling is almost exclusively dependent upon manual labor, thus increasing the cost, particularly given the large number of poultry processed for human consumption on a regular basis. Using feedstuffs can lack precision because the dosage received by any one bird depends both upon the proportion in which the probiotic is mixed with the feed as well as the amount of food that any particular bird eats.

Mixing the probiotic with the drinking water introduces potentially troublesome factors such as water purity and expected differences in water from place to place (i.e. the particular minerals and other items present). Additionally, dilution must be carefully controlled. Perhaps most importantly, certain presently preferred probiotics (including those referred to herein) have a relatively short effective lifetime (sometimes as short as a few minutes) and thus must be ingested rather quickly once presented to the birds. As a result, if the birds fail to drink enough water during the probiotic's effective lifetime, the treatment will have little or no effect.

Furthermore, the difficulties inherent in gavage, feed mixing, or drinking water are exacerbated in very young birds.

Most previous experimentation with spray-applied biologies has involved the use of viral vaccines, such as infectious bronchitis and Newcastle vaccines. As the primary portal of entry for these biologies involves occular or respiratory routes, little research has addressed the conditions necessary for optimal ingestion of spray-applied products. As competitive exclusion cultures apparently must be ingested for optimal colonization of the intestinal tract, modifications of photointensity regimes that favor actual preening activity, and preening as so elated ingestion of spray-applied products, may be important for optimal performance of these cultures.

Competitive exclusion, consisting of undefined adult chicken intestinal microflora, was first described and implemented by Nurmi and coworkers when Salmonella infantis outbreak occurred in Finland; Nurmi, E., and M. Rantala, 1973, *New Aspects of Salmonella Infections in Broiler Production,* Nature 241:210–211. Since then, a variety of delivery systems have been compared and spray application has been demonstrated to be equally protective as drinking water application by several laboratories; Corrier, D. E. et al., 1994, *Competitive Exclusion of Salmonella Enteritidis in Leghorn Chicks; Comparison of Treatment by Crop Gavage, Drinking Water, Spray, or Lyophilized Alginate Beads,* Avian Dis. 38:297–303; Schneitz, C., 1992, Research Note: *Automated Droplet Application of a Competitive Exclusion Preparation,* Poultry Sci. 71:2125–2128; Blankenship, L. C. et al., 1993, *Two-step Mucosal Competitive Exclusion Flora Treatment to Diminish Salmonellae in Commercial Broiler Chickens,* Poultry Sci. 72:1667–1672. Since that time, effective and defined competitive exclusion products have been developed and are commercially available in the United States; Corrier, D. E., et al., 1993, *Development of Defined Cultures of Indigenous Cecal Bacterial to Control Salmonellosis in Broiler Chicks,* Poultry Sc. 72:1164–1168; Corrier, D. E. et al., 1998, *Dosage Titration of a Characterized Competitive Exclusion Culture to Inhibit Salmonella Colonization in Broiler Chickens During Growout;* J. of Food Protection 61:796–801; Hume, M. E. et al., 1998, *Reduction of Caecal Literia Monocytogenes in Leghorn Chicks Following Treatment with a Competitive Exclusion Culture (PREEMPT™),* Letters in Applied Microbiology 26:432–436; Hume, M. E. et al., 1998, *Early Salmonella Challenge Time and Reduction in Chick Cecal Colonization Following Treatment with a Characterized Competitive Exclusion Culture,* J. of Food Protection 61:673–676. Application to large numbers of chicks under commercial conditions must be efficient, should be administered as early in life as possible; Schneitz, C. et al., 1992, *Competitive Exclusion in the Young Bird: Challenge Models, Administration and Reciprocal Protection,* International J. of Food Microbiology, 15:241–244, and should minimize uncontrolled variables such as water quality and proportioner/medicator function and consistency. Automated spray application therefore offers several advantages over drinking water or individual administration by gavage. However, much of the spray-applied product is not ingested by the chick, reducing the percentage of the applied dose that is actually ingested.

Because commercially available defined cultures are relatively expensive to produce under controlled conditions (e.g. PREEMPT™, improved delivery, through enhanced preening activity and preening-associated ingestion of spray-applied product, is an important aspect of commercial use of such products.

Accordingly, a need exists for a method of making sure that very young birds—i.e., chicks—can and will be dosed with sufficient amounts of a desired probiotic to insure that the probiotic has the desired effect against salmonella infection.

OBJECT AND SUMMARY OF THE INVENTION

The foregoing and other objects and advantages of the invention and the manner in which the same are accomplished will become clearer based on the following detailed description taken in conjunction with the accompanying drawings in which:

DETAILED DESCRIPTION

Figure 1:
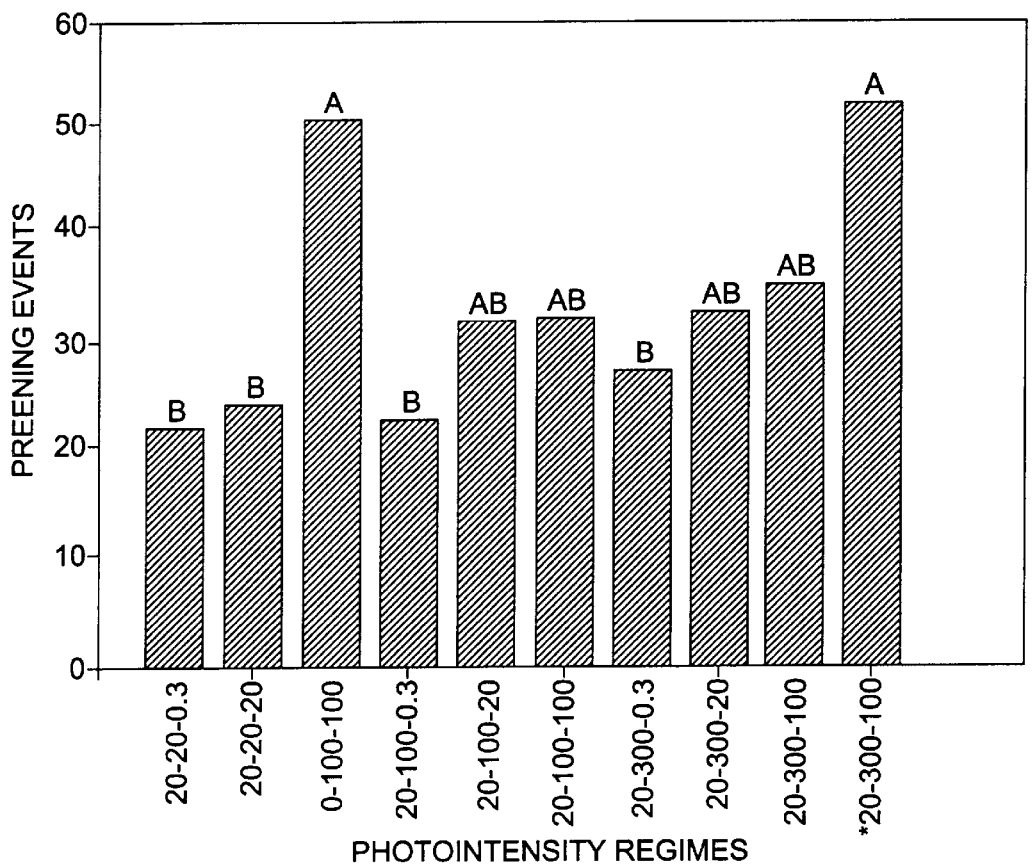
FIG. 1 is a plot of Preening Events versus Photointensity Regimes for various experiments described herein.

In its broadest aspects, the invention is a method of increasing the rate at which young poultry will ingest beneficial probiotic compositions effective against bacteria such as salmonella. In this aspect, the method comprises maintaining a plurality of chicks under an ambient light intensity for a period sufficient for the chicks to acclimate to the ambient light intensity. Thereafter, the method comprises increasing the light intensity to which the chicks are being exposed from the ambient intensity to a predetermined high intensity while distributing a competitive exclusion product onto the chicks and for a time sufficient to spray all the chicks with the competitive exclusion product. Immediately thereafter, the chicks are exposed to an intermediate light intensity that is greater than the ambient intensity but less than the predetermined high intensity for a period substantially equivalent to the effective lifetime of the competitive exclusion product. In preferred embodiments, the step of distributing the competitive exclusion product comprises spraying the chicks with a mixture of water and the competitive exclusion product.

When the invention is used to help prevent salmonella colonization in the birds, the preferred probiotic is that set forth in U.S. Pat. No. 5,478,557 issued to Nisbet et al., the contents of which are incorporated entirely herein by reference. As set forth therein, CE culture used to treat the chicks contains approximately $10^8$ anaerobic cfu/ml, and is added to water at a 1.5 ratio (1 part CE culture with 4 parts water). When using that product in such concentration, the method preferably comprises spraying the mixture in an amount sufficient to provide about 0.25 milliliters (ml) of mixture per chick. Because chicks are typically transported in containers called "flats" that are intended to hold 100 chicks, the method preferably comprises spraying the 100-chick flat with 25.0 ml of the water mixture (in some cases a solution) of competitive exclusion product.

The amount sprayed in total and the amount sprayed per chick can be selected as may be desired or necessary, depending upon the particular probiotic being applied, and can be determined by those of ordinary skill in these arts without undue experimentation. The duration of exposure at both the high and intermediate intensities, the light intensity used, and the sprayed amount of competitive exclusion products are selected to be sufficient to produce an amount of preening in the exposed, sprayed chicks that in turn encourages each chick to ingest an amount of competitive exclusion product that inhibits salmonella colonization in the chicks.

When using the preferred competitive exclusion product set forth in the Nisbet '557 patent, the light intensity and amount of competitive exclusion product are selected to be sufficient to produce an amount of preening in the exposed, sprayed chicks that encourages each chick to ingest an amount of competitive exclusion product that produces propionic acid in the chick in an amount of at least 10 micromoles per gram of cecal content. As set forth in the '559 patent at column 6, line 46 through column 7, line 4, the effectiveness of the competitive exclusion product can be monitored by tracking of both the amount of propionic acid in the cecal contents or by monitoring the total volatile fatty acid concentration.

As set forth in the background, the nature of a competitive exclusion product is such that its effectiveness is against later infection rather than as a remedy for existing problems. Thus, the method preferably comprises treating the birds at a relatively early stage and most preferably when they are chicks between 1 and 14 days old.

FIG. 1 is a chart illustrating the effect of selected photointensity regimes on preening. FIG. 1 plots, in bar graph fashion, the number of preening events measured based on various changes in lighting. As set forth therein, one of the most effective techniques is to keep the chicks in total darkness (a photointensity of 0) and thereafter move them to a photo-intensity of 100 foot candles (FC). As used herein, the foot candle has its accepted definition of a unit of luminance on a surface that is everywhere one foot from a uniform point source of light of one candle and is equal to one lumen per square foot. The unit candle is also referred to as a candela which is the base unit of luminance intensity in the International System of Units and is equal to the luminous intensity in a given direction of a source which emits monochromatic radiation of a frequency of 540 $X^{10}$ hertz and has a radiant intensity in that direction of $\frac{1}{683}$ watt per unit solid angle (cd).

Although movement of the chicks from total darkness to an intensity of 100 foot candles is quite effective in encouraging preening, it raises certain logistical problems. Specifically, the birds must be either kept in total darkness (a generally unworkable arrangement from a practical standpoint) or temporarily housed in some sort of light closet or darkroom for a time sufficient for the chicks to become acclimated after which they can be moved under the 100 foot candle intensity light.

It has been discovered according to the invention, and is set forth graphically on the far right-hand data in FIG. 1, that an effectiveness at least as good as, and in most cases better than, the movement from total darkness to 100 foot candles can be obtained by moving the chicks from an intensity of about 20 foot candles to one of about 300 foot candles while they are being sprayed, followed by an exposure at 100 foot candles for a time sufficient for them to preen the product. The 20 foot candle starting point is particularly advantageous because it represents the generally ambient light intensity for the chicks in their normal growing environment. Similarly, intensities of 300 and 100 foot candles can be relatively straightforwardly arranged using easily available conventional lighting systems.

Accordingly, in a most preferred embodiment, the invention comprises maintaining a flat containing a plurality of chicks at a first position under a light intensity of about 20 foot candles for a period sufficient for the chicks to acclimate to the light intensity. As noted above, this can be accomplished in most cases by simply starting the chicks at their normal surroundings. The method then comprises transferring the flat and the chicks therein to a second position where the light intensity to which the chicks are being exposed is about 300 foot candles. The flat of chicks is sprayed with a mixture of competitive exclusion product and water while the flat and chicks therein are being exposed to the 300 foot candles and immediately thereafter the flat and the chicks therein are transferred to a third position where the chicks are exposed to a light intensity of about 100 foot candles. The flat and the chicks therein are maintained in the third position and exposed to the 100 foot candles for a period substantially equivalent to the effective lifetime of the competitive exclusion product. Where the competitive exclusion product is that set forth in the Nisbet '557 patent, this period will be on the order of about two minutes which is the expected lifetime of the product when applied in the described fashion.

EXPERIMENTAL

The effect of selected sound, photo-intensity, and ambient temperature (TA) changes on preening behavior and ingestion of spray box-applied biologics on day-of-hatch were evaluated. Preening activity was scored by the same individual in all experiments and consisted of the number of total times 5 chicks were observed to preen (preening events) during a 5 minute period immediately following course spray delivery of approximately 3.6 $\mu l/cm^2$ water. Continuous light intensity of 115 FC before and after spraying at a constant 22 C resulted in 2 preening events (PE) observed. Exposure of chicks to relative darkness (<1 FC) for 5 min followed by spray application and increased photointensity of 115 FC resulted in 57 PE observed. Movement of chicks from relative light (5 min., 115 FC) to low light intensity (<1 FC) at the time of spray application resulted in only 5 PE. In all cases, marked changes in sound intensity 64–84 dB, in either direction, reduced preening activity. With constant light (115 FC) and sound (85 dB), increasing ambient temperature (TA) from 22° C. to 35° C. increased PE to 24 as compared to 2 when TA was held at a constant 22C. When fluorescein (1 ug/$\mu l$) in water was applied by spray application (0.2 ml/chick) using 100 day-old-chicks in standard chick trays, quantitation of ingested dye was possible. Briefly, the upper gastrointestinal tract (ventriculus to oropharynx) was dissected from each chick, stomached in 1 ml $H_2O$, and fluorescence compared to a standard fluorescence curve generated by fluorescence analysis of similar contents of gastrointestinal tracts from chicks gavaged with known quantities of dye. In three separate experiments with spray application at the time of change in photointensity, similar results were obtained, resulting in the following average volumes of dye ingested in one minute after spraying: continuous light (115 FC)= 3.85 $\mu l$, dark (<1 FC, 5–15 min) to light (115 FC)=7.21 $\mu l$, light (115 FC) to dark (<1 FC)=3.45 $\mu l$. These data indicate that careful control of environmental conditions is essential for optimal ingestion of spraybox-applied biologics.

In the present experiments, preening behavior of neonatal poults was evaluated using selected photointensity regimes, Studies With Chicks: Experiments with chicks have indicated that increasing photointensity at the time of spray application increases preening activity, as measured by observation and enumeration of preening events (FIG. 1). In these studies, movement of chicks from complete darkness (<0.05 FC) to relatively high photointensity (100 FC, bright laboratory lighting) increased preening activity more than 2-fold. In FIG. 1, the results from several photointensity regime variations are illustrated. Importantly, moving chicks from a common hatchery photointensity of 20 FC, to very bright (300 FC) lighting for 15 seconds at the time of spray, followed by 100 FC lighting for the duration of the 2-minute evaluation period, resulted in preening activity equal to that observed following movement of chicks from complete darkness (>0.05 FC) to bright lighting (100 FC). This photointensity regime eliminates the need to provide a period of complete darkness within the hatchery, while markedly increasing preening activity.

Figure 2:
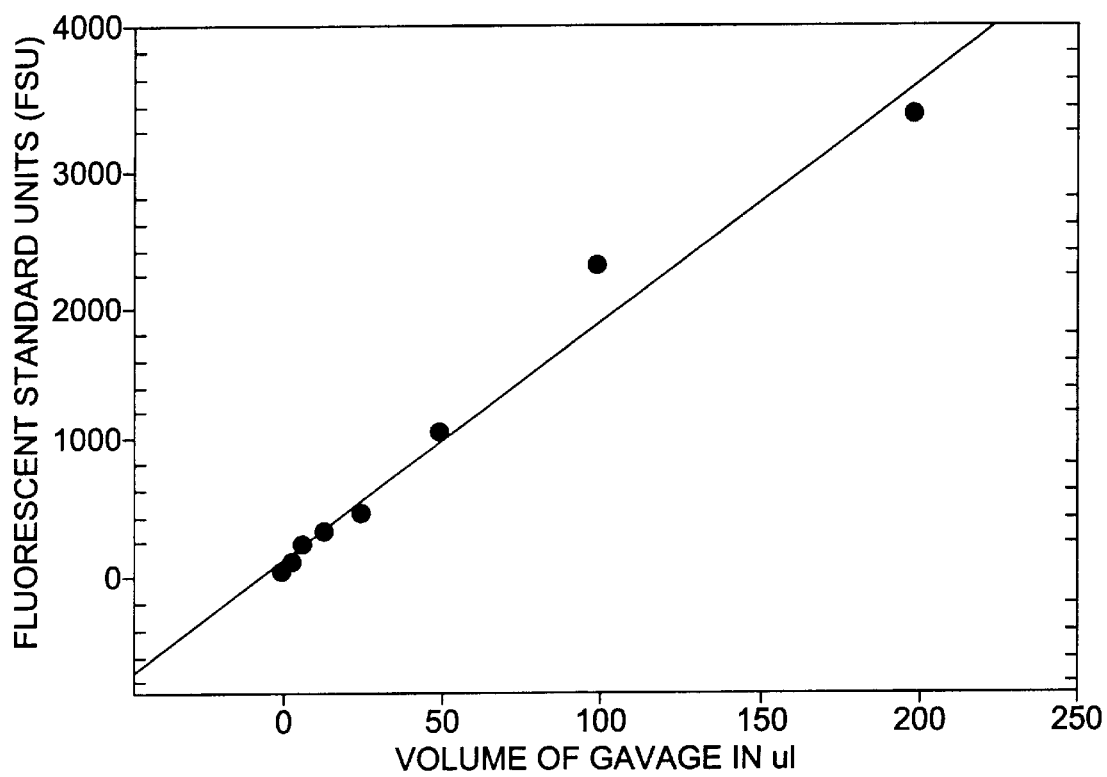
FIG. 2 is a plot of fluorescent standard units versus volume of gavage.

To determine if increased preening activity was associated with actual increased ingestion of spray-applied product, it was necessary to apply a measurable label for quantitative determination of ingestion. For these studies, we initially administered known volumes of fluorescent dye by oral gavage (as described below). Two minutes following administration, chicks were killed and the upper gastrointestinal tract was inspected for travel of the dye. In no case did the dye move caudally past the ventriculus. For this reason, the entire upper gastrointestinal tract was dissected (esophagus to ventriculus), opened, and stomached in a known volume of water. Samples of the resulting solution/suspension were then subjected to quantitative fluorescence and a standard curve was generated. This standard curve was used to determine volumes of ingested spray-applied product in a quantitative manner, using a mathematical model for the generated curve (please see FIG. 2). When volumes of ingested dye were evaluated using those treatments found to increase preening activity (FIG. 1), increased preening was clearly associated with increased ingestion of the spray-applied product (Table 1). FIG. 2 illustrates the relationship of volume of dye administered and fluorescence intensity (fluorescent signal units) recovered from the upper gastrointestinal tract of day-of-hatch chicks. The linear relationship allowed for use as a standard curve for mathematical comparison of unknown samples and estimation of volume ingested (Table 1). Table 1 illustrates the effect of selected photointensity regimes on preening-associated ingestion by day-of-hatch chicks. Volume ingested was mathematically calculated using the standard curve generated following gavage administration of known volumes of fluorescein (FIG. 2).

The following study was performed to determine if similar environmental conditions would increase preening-associated ingestion of spray-applied product in day-of-hatch turkey poults.

Material and Methods

Animals: Poults (straight run) were obtained from a local hatchery and were evaluated on the day-of-hatch (approximately 3–8 hr following hatch) for all experiments.

Poults were killed by $CO_2$ asphyxiation two minutes after spray application except where PREEMPT™ was administered (Experiment 3). For determination of PREEMPT™, establishment as indicated by cecal propionic acid concentrations, chicks were killed 48 hours following placement, as described below.

Experimental Procedures

Figure 3:
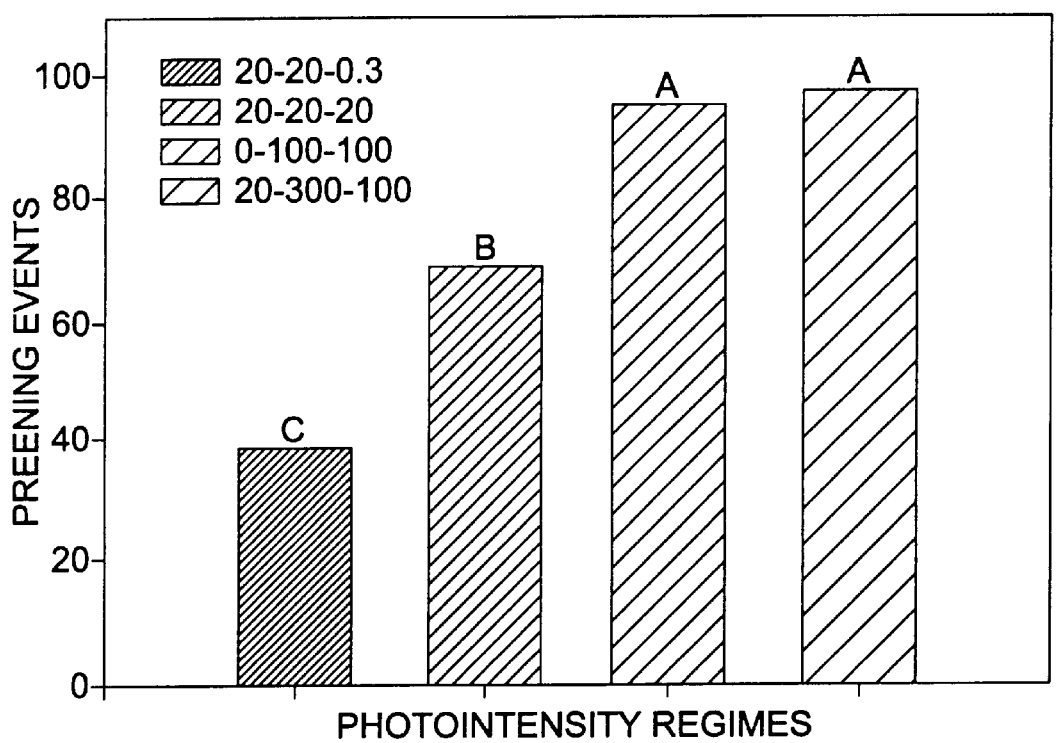
FIG. 3 is a plot of Preening Events versus Photointensity Regimes for various experiments described herein.

Experiment 1: Effects of selected photointensity regimes on preening behavior. (FIG. 3). Selected photointensity regimes were evaluated for effects on preening behavior, enumerated as preening events. For each evaluation, 5 poults were placed in a shallow box (8 cm high with 163 cm² floor) and preening events were enumerated during the first 2 minutes following spray application (manual application of about 3.6 µl/cm² water using a hand-held spray bottle adjusted to a coarse spray, to the entire floor area). Preening events, defined as observed individual acts of pecking/preening of self or other poults (2 minutes, 5 poults/replicate), were enumerated by the same individual in all cases. FIGS. 1 and 3 illustrate the effects of selected photointensity regimes on preening events in neonatal poults. Photointensity regimes are listed below each bar, the first time indicates holding photointensity (FC) 5 minutes prior to spray application. The second time indicates the photointensity at the time of spray application (15 sec). The third time indicates the photointensity during the remainder of the 2-minute period following spray application.

Several hatcheries previously evaluated were illuminated with an approximate photointensity of 20 FC (data not shown). Under this photointensity, the illumination inside stacked chick/poult trays is approximately 0.3 FC. As poults would normally be sprayed under 20 FC and then be moved to the reduced lighting of 0.3 FC in stacked trays after spray application, this treatment served as the baseline control. Because one option is to not immediately stack the trays following spray application, thereby providing a constant photointensity of 20 FC, a second selected treatment consisted of constant 20 FC illumination for the 2-minute period following spray. For the third treatment, known to stimulate chick preening (FIG. 1), poults were held in complete darkness for 5 minutes prior to spray application and maintained under 100 FC for the 2 minutes immediately following spray application. As holding poults under complete darkness until immediately prior to spray application is difficult under commercial conditions, a more convenient photointensity regime was also evaluated, also known to stimulate chick preening. This treatment consisted of 20 FC light exposure prior to spray application, a brief (15 sec) pulse of very bright light (300 FC) at the time of spraying, followed by holding the poults under 100 FC for the duration of the 2 minute period after spray application. The results of this experiment are summarized in FIG. 3.

Figure 4:
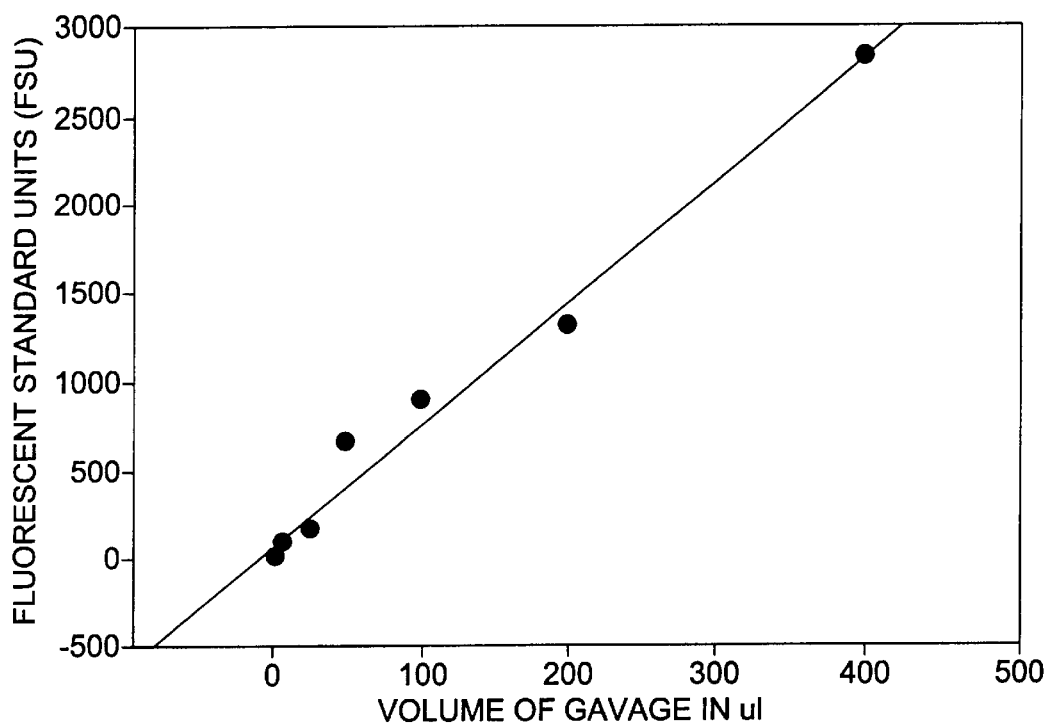
FIG. 4 is a plot of fluorescent standard units versus volume of gavage.

Experiment 2: Effects of selected photointensity regimes on ingestion of fluorescein solution following spray application. (FIG. 4 and Table 2). FIG. 4 illustrates the relationship of volume of dye administered and fluorescence intensity (fluorescent signal units) recovered from the upper gastrointestinal tract of day-of-hatch poults. The linear relationship allowed for use as a standard curve for mathematical comparison of unknown samples and estimation of volume ingested (Table 1).

Table 2 lists the effect of selected photointensity regimes on preening-associated ingestion by day-of-hatch poults. Volume ingested was mathematically calculated using the standard curve generated following gavage administration of known volumes of fluorescein (FIG. 2).

TABLE 1

| Group | FC 5 Min. Before Spray | FC 5 Min. After Spray | Fluorescein Ingested (µl) 2 Min. |
|---|---|---|---|
| 1 | 115.5 | 115.5 | 3.222 |
| 2 | 0 | 115.5 | 2.771 |
| 3 | 115.5 | 0 | 1.00 |
| 4 | 0 | 115.5 | 4.427 |

TABLE 2

| Group | FC 5 Min. Before Spray | FC 5 Min. After Spray | Fluorescein Ingested (µl) 2 Min. |
|---|---|---|---|
| 1 | 20 | 20 | 26.32 |
| 2 | 0.0 | 100 | 42.29 |
| 3 | 20[1] | 100 | 49.66 |
| 4 | 20[2] | 100 | 59.46 |

[1]Pulsed for 30 sec. at 300 FC at time of spray.
[2]Pulsed for 15 sec. at 300 FC at time of spray.

To determine the actual volume of spray-applied product ingested by poults, fluorescein was incorporated as a label in the spray. Known volumes of the labeled water were administered by gavage, followed by termination and dissection of the upper gastrointestinal tract (esophagus-ventriculus) 2 minutes after administration. Each removed portion of the upper gastrointestinal tract was opened and the tissue and contents were combined with 1.0 ml deionized $H_2O$ in an individual Whirl Pac bag. The contents were then stomached for 1 minute. The resulting suspension/solution (50 µl) of each sample was transferred to a 96 well polystyrene plate for determination of fluorescent signal units using an automated fluorescence spectrophotometer (Dynex Flurolite 1000, excitation 485 nm and emission 515 nm). This data was used to generate a standard curve (FIG. 4), against which, unknown values were mathematically compared for conversion to volumes of ingested fluorescein solution following spray application (Table 2).

Figure 5:
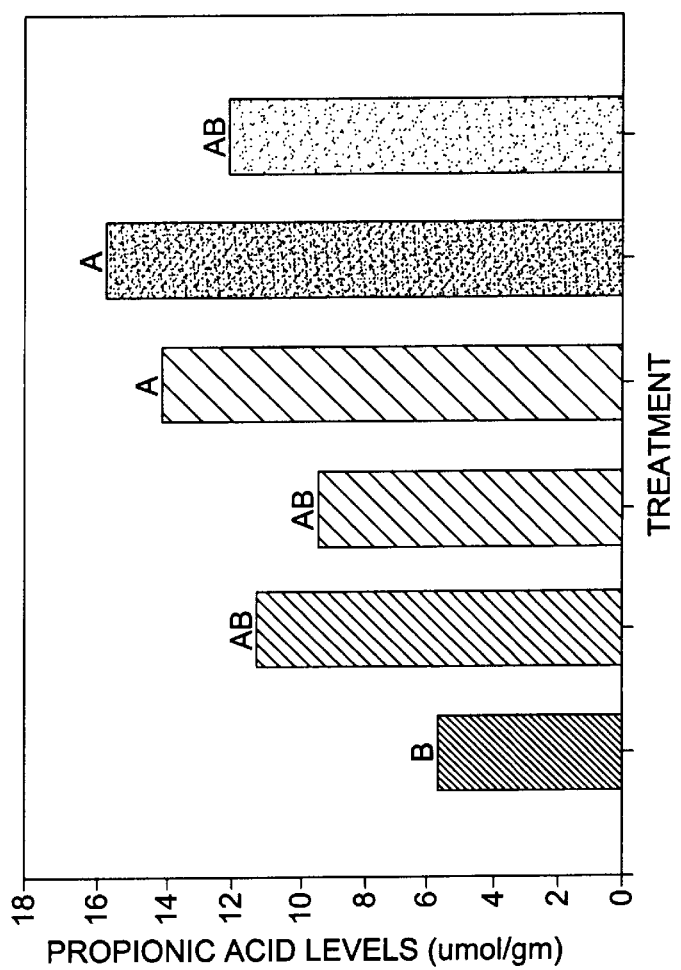
FIG. 5 is a plot of propionic acid levels for several treatment regimes.

Experiment 3: Effects of selected photointensity regimes on establishment of CE culture (FIG. 5). FIG. 5 illustrates the effect of selected treatments on establishment of CE culture, PREEMPT™, as determined by cecal propionic acid concentration 48 hours following poult placement. PREEMPT™ was administered either before or after a 16 hour holding time. Treatments included no treatment, gavage administration, or spray application. Poults were held at 20 FC for 5 minutes prior to spray application, 300 FC at the time of spray application (15 sec) and 100 FC for the duration of the 2-minute period following spray application. PREEMPT™ administration in the drinking water during the first 4 hours of placement time was also compared.

Because many commercial poult hatcheries hold newly hatched poults for about 16 hours prior to placement, the following experiment was implemented to determine whether optimal PREEMPT™ establishment would occur following administration immediately following hatch, or immediately following the 16 hour holding period. All poults were held for 16 hours, in total darkness, prior to placement in this study. Treatments consisted of spray-application at hatch (manufacturers directions), gavage, spray application following 16 hours of holding time (darkness), and drinking water administration (I dose/25 ml, provided for 4 hours). Each treatment was applied to 25 poults. Approximately 16 hours following initial treatment, poults were placed in floor pens on new pine shavings, with water and feed (formulated to meet or exceed NRC recommendations for started poults) provided ad libitum. Forty-eight hours following poult placement, poults were killed and individual cecal contents (0.2 g of cecal contents plus 1.8 ml of $H_2O$) were collected in sealed polypropylene tubes which were maintained at $-70$" C. prior to VFA profile analysis by gas chromatography, as previously described by Corrier et al. in the references cited herein.

Statistical Analysis: Means were compared using analysis of variance and significant differences ($P \leq 0.05$) were further separated using Duncan's multiple range test. See, SAS Institute 1987, *SAS/STAT Guide for Personal Computers*, $6^{th}$ Ed., SAS Institute Inc., Cary, N.C.; Duncan, D. B., 1955, *Multiple Range and Multiple F Tests*, Biometrics 11:1–42.

Results and Discussion

Experiment 1 (FIG. 3): As noted in previous studies with chicks (see FIG. 1), altering the photointensity regimes near the time of spray application to neonatal poults caused marked effects on preening activity. In this experiment, maintaining, chicks under normal hatchery photointensity (about 20 FC) prior to, and during spray application, followed immediately by the photointensity found in stacked chick/poult trays (0.3 FC) resulted in less than 40 preening events during the 2 minute time period following spray application. Holding and maintaining chicks at 20 FC prior to and following spray application significantly increased preening activity (>50%). Holding the chicks in total darkness for 5 minutes prior to spray application, followed by illumination at 100 FC for spray application and the 2 minute post-spray evaluation time, markedly and significantly increased (>2-fold) preening activity. Interestingly, poults that were maintained at normal hatchery photointensity (20 FC) prior to spray application could be induced to preen with an intensity equal to those held in complete darkness. In this case, poults were briefly exposed to very bright halogen lighting (300 FC) at the time of spray application (15 seconds) and then moved to an area with 100 FC for the remaining 1.75 minutes. This later photointensity regime offers near-optimal induction of preening with minimal disruption of hatchery practices or facilities.

Experiment 2 (FIG. 4, Table 2): This experiment was initiated to determine whether there is an association between observed preening activity and actual ingestion of spray-applied product. In this experiment known volumes of fluorescein solution were administered by gavage to 5 poults per volume. Two minutes following gavage, poults were killed and the upper gastrointestinal tract was removed by dissection, incised, and individually placed in Whirl Pac bags with 1.0 ml water. Each bag was stomached and 50 $\mu$l of the resulting solution/suspension was placed in each well of a 96 well polystyrene plate for fluorescence analysis as described above. This allowed for generation of a curve representing the relationship between fluorescence intensity and volume ingested and thus served a standard curve for mathematical comparison (FIG. 4). When poults were subjected to spray application of the same concentration of fluorescein dye, resulting fluorescence activity could be compared to the standard curve for determination of ingested volume (Table 2). Similar to the effect of increasing photointensity on preening activity (FIG. 3), increasing photointensity at the time of spray application from either 0.0 FC or 20 FC to 100 FC at the time of spray application through the 2 minutes following spray application, resulted in approximately two-fold increases in the actual volume ingested. The data also suggest a small benefit to brief exposure to 300 FC at the time of spray application.

Experiment 3 (FIG. 5): In many turkey hatcheries, poults are held overnight (about 16 hours) prior to placement. As such, PREEMPT™ could be administered either immediately prior to poult holding or 16 hours later near the time of placement. In the present experiment, spray application, using the near-optimal photointensity regime established in Experiment 2 (20 FC prior to spray, 300 FC at the time of spray (about 15 sec), followed by 100 FC for the remaining 1.75 minutes), caused establishment of PREEMPT™, as measured by 48 hour cecal propionate levels, with equal effect as compared to gavage. This was true whether PREEMPT™ was administered before or after the 16 hour poult holding time. Cecal propionate concentrations were generally higher when PREEMPT™ was administered following the 16 hour holding time. Drinking water administration, at the time of poult placement, resulted in 48 hour cecal propionate concentrations that were not significantly different to either spray application or gavage ach-ninistration of PREEMPT™.

Figure 6:
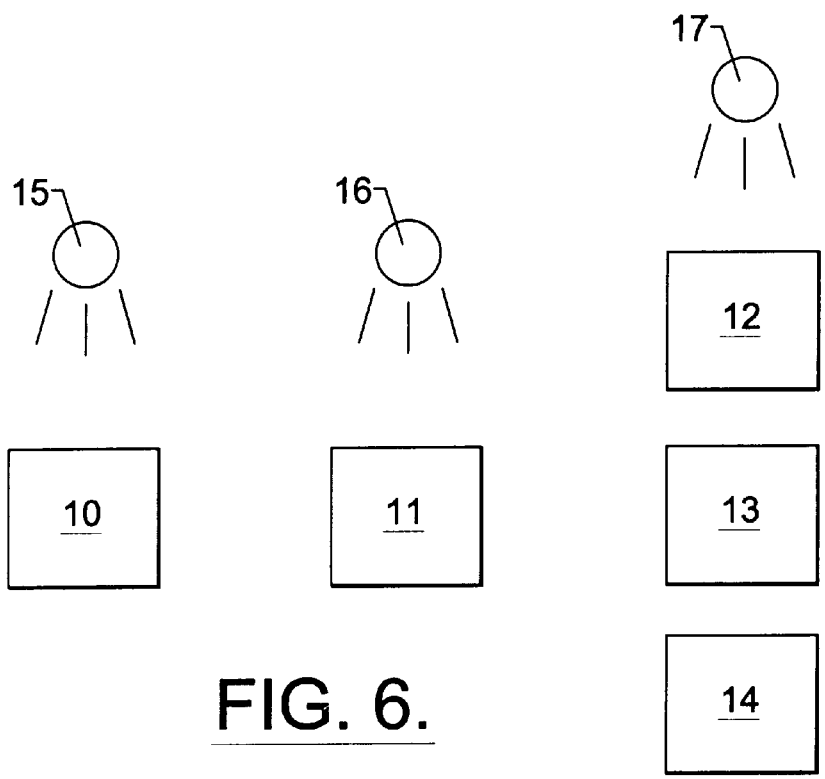
FIGS. 6 and 7 are schematic diagrams of the method of the invention.

Conclusions: These data confirm that PREEMPT™ was efficacious in turkey poults, Hollister, A. G. et al., 1994, *Comparison of effects of chicken cecal microorganisms maintained in continuous culture and provision of dietary lactose on cecal colonization by Salmonella typhimurium in turkey poults and broiler chicks*, Poultry Sci. 73:640–647. Also, these data indicate that increasing photointensity at the time of spray application increases poult preening activity, increases actual volume of ingested spray-applied product, and increases establishment of PREEMPT™, as measured by 48 hour cecal propionate levels. While these data indicate that PREEMPT™ application can be efficacious when administered immediately following hatch, there is some indication of improved establishment of the culture if administration is delayed until after the 16 hour holding period, near the time of poult placement, FIGS. 6 and 7 help illustrate the relatively straightforward manner in which the method of the invention can be carried out. FIG. 6 schematically illustrates a plurality of flats 10–14 which are typically used to carry 100 chicks. Three light sources 15–17 respectively illustrate the flats at different steps in the method. In particular, the first light source 15 illustrates the flat 10 that is under the ambient lighting conditions, and thus the first light source 15 preferably has an intensity of about 20 foot candles.

The next flat 11 is illustrated by the second light source 16 which is the light source that provides the predetermined higher intensity, preferably approximately 300 foot candles.

The third light source 17 illuminates a total of three (or more) flats that are under the intermediate light intensity that is greater than the ambient intensity but less than the predetermined high intensity, preferably about 100 foot candles.

Figure 7:
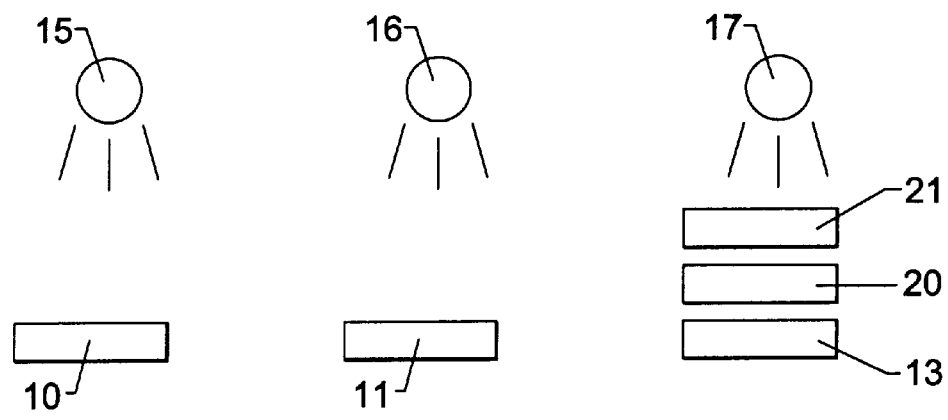

FIG. 7 illustrates the manner in which the flats and the chicks therein are maintained in the third position and exposed to the intermediate light intensity for a period substantially equivalent to the effective lifetime of the competitive exclusion product. FIG. 7 illustrates the same first, second, and third light sources 15, 16, and 17, respectively. Similarly, FIG. 7 illustrates five flats 10, 11, 13, 20, and 21. The fourth and fifth flats 20 and 21 are illustrated as being stacked on top of flat 13 under the intermediate light source 17. It has been found according to the present invention that a straightforward method of making sure that the chicks remain under the intermediate light source for the appropriate time period is to simply lay out the flats in the manner shown in FIG. 6, and then sequentially stack them, covering each flat horizontally before starting a new vertical row, in the manner shown in FIG. 7.

Figure 8:
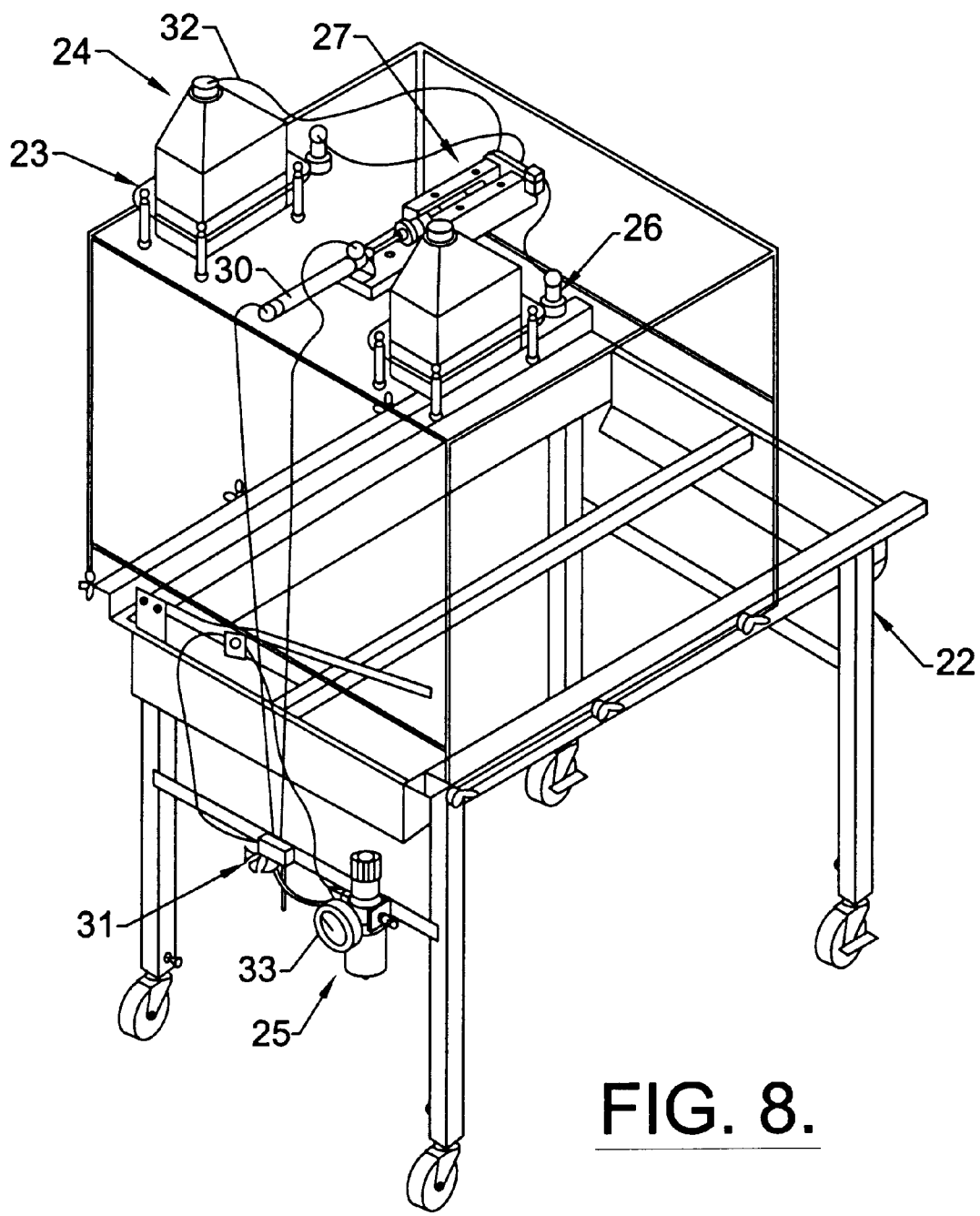
FIG. 8 is a perspective view of an apparatus according to the present invention.

In another aspect, the invention comprises an apparatus for carrying out the method of the invention. FIG. 8 illustrates an embodiment of such a device. In the illustrated embodiment, the apparatus includes a stainless steel base 22, a cabinet 23 on the base 22 with the cabinet preferably being formed of an appropriate polymer such as a polycarbonate resin, at least one, and as illustrated two, containers 24 for the supply of competitive exclusion which is to be sprayed, a metering means shown as the four-way valve 25, and a spray nozzle 26 in fluid communication with each of the containers 24.

The metering means further includes a syringe 27 mounted on top of the cabinet 23 which is controlled by the stroke cylinder 30 which is driven by air pressure from a local supply (not shown) and controlled by the valve 25 and its relief valve 31.

In operation, the various hoses and hose fittings illustrated in FIG. 8 (which are otherwise conventional and will not be described in detail) are securely fastened. A new syringe 27 is periodically replaced, typically at the beginning of a workday. To date, it has been found that conventional syringes have a life span of between about 20,000 and 30,000 doses and it is recommended that the syringe accordingly be replaced after about 20,000 doses.

The syringe is driven by a line of pressurized air at a pressure of about 60 psi. The hose 32 that goes into the container 24 (and to the syringe 27) should be placed at the bottom of the container 24 to avoid drawing air into the spray line. In order to measure the spray volume, a calibrated container can be placed under each nozzle following which the spraying mechanism is triggered. An appropriate volume can then be measured, and is typically between about 12 and 13 ml for each nozzle.

The volume delivered by the syringe 27 can be adjusted by speeding up or slowing the syringe refill time using the valve 25 associated with the pressure gauge 33 on the cabinet. Because the reconstitution solution tends to generate gas, the preferred competitive exclusion product tends to foam when agitated. The foaming can be caused or exacerbated by a relatively fast syringe refill time. This can undesirably alter the amount of product drawn into the syringe, but can be corrected by typically slowing the syringe refill speed. As a rule of thumb, the syringe refill time should equal the time it takes to re-stack the boxes and be prepared to spray the next box; e.g., as illustrated in FIGS. 6 and 7.

The lighting apparatus is placed directly over the spray box and preferably provides approximately 300–400 foot candles of light to stimulate the birds. Dual halogen lighting apparatuses are presently preferred for this purpose.

As schematically illustrated in FIGS. 5 and 6, a second lighting apparatus is used where the chicks are re-stacked. In a typical procedure, four dollies are placed directly underneath the lighting apparatus to raise it approximately 6 feet above the flats. This reduces the light intensity as compared to the spray cabinet and provides the desired illumination of approximately 100–200 foot candles. This also increases product visibility and decreases the chick drying time. As noted above, when re-stacking, a chick box is placed on each of the dollies before placing another on the initial box that was placed. In a typical embodiment, the procedure is continued in that order until 10 boxes are reached on all four dollies. The goal is to keep the chicks under the bright lighting on the dollies for approximately one minute.

In the drawings and specification, there have been disclosed typical embodiments of the invention, and, although specific terms have been employed, they have been used in a generic and descriptive sense only and not for purposes of limitation, the scope of the invention being set forth in the following claims.

What is claimed is:

1. A method of increasing the rate at which chicks will ingest a competitive exclusion product effective against salmonellae, the method comprising:

maintaining a plurality of chicks under the ambient light intensity for the chicks in their normal growing environment for a period sufficient for the chicks to acclimate to the ambient light intensity, and with the proviso that the ambient light intensity is other than darkness;

increasing the light intensity to which the chicks are being exposed from the ambient intensity to a predetermined intensity higher than the ambient intensity while distributing a competitive exclusion product onto the chicks and for a time sufficient to spray all of the chicks with the competitive exclusion product; and immediately thereafter exposing the chicks to an intermediate light intensity that is greater than the normal growing environment ambient intensity but less than the predetermined higher intensity for a period substantially equivalent to the effective lifetime of the competitive exclusion product.

2. A method according to claim 1 wherein the step of distributing the competitive exclusion product comprises spraying the chicks with a mixture of water and competitive exclusion product.

3. A method according to claim 2 comprising spraying the mixture in an amount sufficient to provide about 0.25 milliliters of mixture per chick.

4. A method according to claim 2 wherein the duration of exposure, the light intensity, and the sprayed amount of competitive exclusion product are sufficient to produce an amount of preening in the exposed, sprayed chicks that in turn encourages each chick to ingest an amount of competitive exclusion product that inhibits salmonella colonization in the chicks.

5. A method according to claim 2 wherein the duration of exposure, the light intensity, and the amount of competitive exclusion product are sufficient to produce an amount of preening in the exposed, sprayed chicks that in turn encourages each chick to ingest an amount of competitive exclusion product that produces propionic acid in the chick in an amount of at least about 10 micromoles per gram of cecal content.

6. A method according to claim 1 that is carried out on chicks that are between 1 and 14 days old.

7. A method of increasing the rate at which chicks will ingest a competitive exclusion product effective against salmonellae, the method comprising:

maintaining a flat containing a plurality of chicks at a first position under the ambient light intensity for the chicks in their normal growing environment for a period sufficient for the chicks to acclimate to the ambient light intensity, and with the proviso that the ambient light intensity is other than darkness;

transferring the flat and the chicks therein to a second position where the light intensity to which the chicks are being exposed is at a predetermined higher intensity than the normal growing environment ambient intensity;

distributing a competitive exclusion product onto the flat of chicks while the flat and chicks therein are being exposed to the higher intensity light at the second position; and immediately thereafter transferring the flat and the chicks therein to a third position where the chicks are exposed to an intermediate light intensity that is greater than the normal growing environment ambient intensity but less than the predetermined high intensity; and maintaining the flat and the chicks therein in the third position and exposed to the intermediate light intensity for a period substantially equivalent to the effective lifetime of the competitive exclusion product.

8. A method according to claim 7 wherein the step of distributing the competitive exclusion product comprises spraying the flat with a mixture of water and competitive exclusion product in an amount sufficient to distribute the competitive exclusion product on substantially all of the chicks.

9. A method according to claim 8 wherein the duration of exposure and the light intensity are sufficient to produce an amount of preening in the exposed, sprayed chicks that encourages each chick to ingest an amount of competitive exclusion product that inhibits salmonella colonization in the chicks.

10. A method according to claim 8 wherein the duration of exposure, the light intensity, and the amount of competitive exclusion product are sufficient to produce an amount of preening in the exposed, sprayed chicks that encourages each chick to ingest an amount of competitive exclusion product that produces propionic acid in the chick in an amount of at least about 10 micromoles per gram of cecal content.

11. A method according to claim 8 comprising spraying a flat containing about 100 chicks with about 25 milliliters of the mixture.

12. A method according to claim 7 comprising allowing the chicks to dry following the step of exposing them to the intermediate light intensity.

13. A method according to claim 7 that is carried out on chicks that are between 1 and 14 days old.

14. A method of increasing the rate at which chicks will ingest a competitive exclusion product effective against salmonellae, the method comprising:

maintaining a plurality of chicks under light having an intensity of about 20 foot candles for a period sufficient for the chicks to acclimate to such light intensity;

thereafter exposing the plurality of chicks to light of an intensity of between about 300 and 400 foot candles while spraying the chicks with a mixture of water and a competitive exclusion product; and immediately thereafter maintaining the chicks under light of an intensity of between about 100 and 200 footcandles for a period of 2 minutes.

15. A method according to claim 14 comprising spraying the chicks under a light intensity of about 300 foot candles.

16. A method according to claim 15 wherein the chicks are thereafter maintained under a light intensity of about 100 foot candles.

17. A method according to claim 15 comprising spraying the mixture in an amount sufficient to provide about 0.25 milliliters of mixture per chick.

18. A method according to claim 14 wherein the duration of exposure, the light intensity, and the amount of competitive exclusion product are sufficient to produce an amount of preening in the exposed, sprayed chicks that in turn encourages each chick to ingest an amount of competitive exclusion product that inhibits salmonella colonization in the chicks.

19. A method according to claim 14 wherein the duration of exposure, the light intensity, and the amount of competitive exclusion product are sufficient to produce an amount of preening in the exposed, sprayed chicks that in turn encourages each chick to ingest an amount of competitive exclusion product that produces propionic acid in the chick in an amount of at least about 10 micromoles per gram of cecal content.

20. A method according to claim 14 that is carried out on chicks that are between 1 and 14 days old.

21. A method of increasing the rate at which chicks will ingest a competitive exclusion product effective against salmonellae, the method comprising:

maintaining a flat containing a plurality of chicks at a first position under a light intensity of about 20 foot candles for a period sufficient for the chicks to acclimate to such light intensity;

transferring the flat and the chicks therein to a second position where the light intensity to which the chicks are being exposed is about 300 foot candles;

spraying the flat of chicks with a mixture of competitive exclusion product and water while the flat and chicks therein are being exposed to the 300 foot candles; and immediately thereafter transferring the flat and the chicks therein to a third position where the chicks are exposed to a light intensity of about 100 foot candles; and maintaining the flat and the chicks therein in the third position and exposed to the 100 foot candles for a period substantially equivalent to the effective lifetime of the competitive exclusion product.

22. A method according to claim 21 wherein the step of spraying the flat comprises spraying with an amount of competitive exclusion product sufficient to distribute the competitive exclusion product on substantially all of the chicks.

23. A method according to claim 22 wherein the step of spraying the flat comprises spraying with an amount of competitive exclusion product that produces propionic acid in the chick in an amount of at least about 10 micromoles per gram of cecal content.

24. A method according to claim 21 comprising spraying a flat containing about 100 chicks with about 25 milliliters of the mixture.

25. A method according to claim 21 comprising allowing the chicks to dry following the step of exposing them to the intermediate light intensity.

26. A method according to claim 21 that is carried out on chicks that are between 1 and 14 days old.

* * * * *